(12) United States Patent
Bardelli et al.

(10) Patent No.: US 10,682,123 B2
(45) Date of Patent: *Jun. 16, 2020

(54) METHOD OF SETTING A WAVEFORM SIGNAL IN AN ULTRASOUND IMAGING APPARATUS AND APPARATUS FOR SETTING AN ULTRASONIC WAVEFORM SIGNAL USING SUCH METHOD

(71) Applicant: STMicroelectronics, Agrate Brianza (IT)

(72) Inventors: Roberto Giorgio Bardelli, Fino Mornasco (IT); Stefano Passi, Pavia (IT)

(73) Assignee: STMicroelectronics S.r.l, Agrate Brianza (IT)

( * ) Notice: Subject to any disclaimer, the term of this patent is extended or adjusted under 35 U.S.C. 154(b) by 203 days.

This patent is subject to a terminal disclaimer.

(21) Appl. No.: 15/849,040

(22) Filed: Dec. 20, 2017

(65) Prior Publication Data

US 2018/0177494 A1    Jun. 28, 2018

Related U.S. Application Data

(63) Continuation of application No. 14/263,311, filed on Apr. 28, 2014, now Pat. No. 9,877,703.

(30) Foreign Application Priority Data

Apr. 30, 2013  (IT) .............................. MI2013A0701

(51) Int. Cl.
*A61B 8/08*    (2006.01)
*A61B 8/00*    (2006.01)
*G01S 7/52*    (2006.01)

(52) U.S. Cl.
CPC .......... *A61B 8/5292* (2013.01); *A61B 8/4494* (2013.01); *A61B 8/5207* (2013.01); *A61B 8/54* (2013.01); *G01S 7/5202* (2013.01)

(58) Field of Classification Search
CPC ... A61B 8/5292; A61B 8/4494; A61B 8/5207; A61B 8/54; G01S 7/5202; G01K 11/346
See application file for complete search history.

(56) References Cited

U.S. PATENT DOCUMENTS

| | | |
|---|---|---|
| 6,115,324 A | 9/2000 | Lillegard |
| 6,551,244 B1 | 4/2003 | Gee |
| 9,162,255 B1 | 10/2015 | Stice et al. |
| 2011/0060225 A1 | 3/2011 | Cogan et al. |

FOREIGN PATENT DOCUMENTS

| | | |
|---|---|---|
| EP | 2 209 019 A1 | 7/2010 |
| JP | 2006-149503 A | 6/2006 |

*Primary Examiner* — Jeffrey G Hoekstra
*Assistant Examiner* — Katherine M McDonald
(74) *Attorney, Agent, or Firm* — Seed IP Law Group LLP

(57) ABSTRACT

A digital representation of a waveform is generated based on signals received during a recording period. The received signals include a digital clock signal providing a determined number of clock pulses during the recording period, a plurality of binary digital signals defining, for each clock pulse of the determined number of clock pulses, a waveform state associated with the clock pulse. A digital representation of the waveform is generated and stored. The waveform has a duration based on the recording period and a profile based on the defined waveform states associated with the clock pulses of the determined number of clock pulses.

25 Claims, 9 Drawing Sheets

METHOD OF SETTING A WAVEFORM SIGNAL IN AN ULTRASOUND IMAGING APPARATUS AND APPARATUS FOR SETTING AN ULTRASONIC WAVEFORM SIGNAL USING SUCH METHOD

BACKGROUND

Technical Field

The present disclosure is directed to a method of setting a waveform signal in an apparatus for ultrasound applications and an apparatus for generating ultrasounds using such method.

The present disclosure is directed to a method and a device that are configured to generate an ultrasonic waveform signal (hereinafter briefly referred to as acoustic signal) for use in an apparatus for ultrasound applications.

Description of the Related Art

An apparatus for ultrasound applications is, for instance, an ultrasound or sonographic machine that may comprise a medical diagnostic testing system that uses ultrasonic waves or ultrasounds and is based on the principle of ultrasound transmission and echo emission analysis. Such apparatuses are widely used in internal medicine, surgery and radiology.

In such machine, the acoustic signal is directed to a target region, for example, in the human body, for 2D or 3D scanning, and when the acoustic signal impinges upon such region, the apparatus receives the reflected acoustic signal and processes it to generate the 2D/3D image on a screen.

It shall be noted that the present disclosure also applies to any system that may be used to acquire an arbitrary waveform signal. This signal may be of analog type, converted by a transducer into an analog electrical signal and then converted by an n-bit ADC (Analog-to-Digital Converter) into n digital electrical signals, before being acquired by recording, otherwise it may be directly of digital electrical type. The signal so recorded and stored may be used to control actuators for ultrasound applications, not necessarily piezoelectric actuators, but also optical, mechanical or other types of actuators, as used in contexts such as telecommunications or industrial automation.

A variety of types of integrated circuits (ASIC) are known in the art, which facilitate configuration, delaying and generation of distinct acoustic signals for use in an ultrasound imaging apparatus.

For example, referring to FIG. 1, which shows a block diagram of an integrated circuit for use in a prior art apparatus for ultrasound applications, an interface 1 is shown, which receives a waveform signal WF with a preset duration $T_{WF}$ and is in signal communication with a first functional block 2, that acts as a unit for generating an acoustic signal profile, and with a second functional block 3 that is in signal communication with both the functional block 2 and the interface 1 and acts as a unit for setting phase delays of the acoustic signal.

Acoustic signals are generated through a plurality of transducer elements 5, which are configured to transmit their respective acoustic signals to the selected target region and to later receive the reflected acoustic signal.

It may be further noted that the device comprises a third functional block 4, which is in signal communication with the second block 2 and acts as a waveform pulse generator, and with a plurality of transducers 5, each receiving the pulse of the acoustic signal to be generated from said third functional block 4.

For example, the interface 1 is a serial interface and uses an appropriate data transmission protocol to transfer the bits 2A to configure the acoustic signal profile to the functional block 2 and the bits 2B for setting phase delays to the functional block 3.

The functional block 3 receives the acoustic signal profile generated by the block 2, replicates it for each transducer and associates a phase delay with each copy.

Each of these signals is emitted through the functional block 4 to its respective transducer 5.

Two approaches are used to store the waveforms to be generated. The first approach uses a first serial communication to store the basic waveforms containing a single state, the time during which such state remains, and a relative index. Then, it uses a second serial communication to store a sequence of indices describing the sequence of basic waveforms that form the entire waveform.

This system provides good versatility but requires additional information (the sequence of indices), which involves higher area usage and two communication operations with the serial interface that require longer setup times.

For example, in order to store the waveform of FIG. 6A, 2 bits will be required to describe one of the 4 states, 3 bits will be required to store the state maintenance time (8 units max) and 4 bits will be required to associate an index with the 13 basic waveforms. As a whole, the storage of this simple waveform will require (2+3+4)×13=117 bits. The second approach consists in storing the parameters that describe the waveform as a whole, e.g., the number and duration of pulses. This system affect flexibility in waveform configuration to prevent excessive memory usage, and hence excessive area usage.

For example, a maximum number of pulses will be limited to Ni, and configuration will be limited to the durations of the first and last pulses, and an identical duration for all the others, the sequence of states being fixed to a given non-configurable sequence.

Obviously, storage limited to simple waveforms like the ones of FIG. 4 can be stored, and waveforms like that of FIG. 6A cannot be stored.

It will be understood that, with the clock frequencies that are usually employed in these systems, e.g., from 50 to 200 MegaHertz, the time required for transfer of the bits required to set the profile and the phase delays becomes a significant consideration.

This is even truer when considering the need of setting different acoustic signal profiles.

Indeed, as the number of acoustic signal profiles employed for scanning increases, a longer time is needed to configure the system by setting all the descriptive parameters of the different waveforms in use.

This is due to the need of storing the profile of the acoustic signal to be emitted.

For example, in a system with 200 MHz clock, 177 flip-flops would be used to store the profile of an acoustic signal like that of FIG. 6A, having a duration of 115 nsec. In the first prior art approach the time for configuration includes two serial communications with a header time imposed by the selected profile. These operations are used to fill both the actually employed 117 flip-flops and, for the purpose of configuration of the whole system and compliance with the selected protocol, possibly also unused flip-flops.

The minimum time will be: $T_{conf} = 117 \times 5$ ns $+ 2 \times T_{heater}$.

It shall be noted that the possibility of having a wide choice in setting different profiles and acoustic signal delays will afford a higher accuracy of the images of the object to be scanned.

BRIEF SUMMARY

In one embodiment, a method may be provided that facilitates reducing the bit rates, facilitating setting different acoustic signal profiles in a dramatically shorter time than in prior art systems.

Furthermore, in one embodiment, a negligible increase of circuit complexity may improve bit rate performance and memory savings.

In an embodiment, the method is applicable irrespective of the protocol implemented by the interface, as it is independent thereof.

In an embodiment, a method of setting a waveform signal in an ultrasound imaging apparatus comprises: providing a waveform signal having a preset duration and a preset profile, said profile defining a plurality of operating states, said method including providing a digital clock signal defining a number of clock pulses in a determined period; providing at least one first and one second digital signals, each defining two operating states; associating each operating state of said plurality of operating states with a combination of said two operating states of said at least one first and one second digital signals; storing said combination of said two operating states of said at least one first and one second digital signals, thereby generating a combination sequence whose duration is equal to the preset duration of said waveform signal; said combination sequence comprising a number of combinations of said two operating states of said at least one first and one second digital signals, which is equal to the number of clock pulses in said preset duration of said waveform signal. In an embodiment, each of said operating states of said digital waveform signal has its own duration; said combination sequence comprising a number of combinations of said two operating states of said at least one first and one second digital signals, which is equal to the number of clock pulses in said duration of each of said operating states of said waveform signal. In an embodiment, the method comprises: determining a value representative of the number of clock pulses in said duration of each operating state of said plurality of operating states of said digital waveform signal according to the rate of said clock frequency; associating said value representative of the number of clock pulses with each operating state of said plurality of operating states of said digital waveform signal; said combination sequence comprising a number of said two operating states of said at least one first and one second digital signals, which is equal to the value representative of the number of clock pulses for each operating state of said plurality of operating states of said digital waveform signal. In an embodiment, the method comprises: determining when two or more adjacent operating states of said at least one first signal and said second signal have synchronous changes; determining a state permanence value defining the time in said duration during which each operating state of said plurality of operating states of said digital waveform signal remains, when said two operating states of said at least one first and one second digital signals coincide, according to the rate of said clock frequency; storing a single repetition and the repetition rate of the combination of operative states of said at least one first and said second digital signals. In an embodiment, the method comprises: providing a third digital signal defining two operating states, said step of storing said digital waveform coded signal starting at the start of the first operating state of said two operating states of said third signal and ends at the start of the second operating state of said two operating states of said third signal. In an embodiment, the method comprises: sending said digital waveform coded signal to an ultrasound generator.

In an embodiment, a device for setting a waveform signal in an ultrasound imaging apparatus comprising a plurality of transducers, each being operatively configured to generate an ultrasonic waveform signal, comprises: a phase shift unit operatively configured to receive at least one characteristic phase delay parameter of said waveform signal and to generate a phase delay, said phase shift unit being in signal communication with each transducer of said plurality of transducers to send said phase delay to each transducer; a storage unit configured to receive at least one digital clock signal defining a number of clock pulses in a determined period and at least one first and one second digital signals whose combination defines a combination sequence, and configured to generate said combination sequence, said storage unit being in signal communication with each transducer of the plurality of transducers to transmit the combination sequence, said storage unit comprising: compression means configured to sample the changes of the operating states of said sequence of combination sequence according to said digital clock signal; a first memory table configured to store said changes of the operating states of said sequence of combination sequence; a first counter for storing the time between two continuous events of said sequence of combination sequence; said phase shift unit comprising: a second memory table configured to store phase delays for each transducer of said plurality of transducers; a second counter for storing the occurrences of said phase delay value being reached by the delay counter; each transducer of said plurality of transducers comprising its own counter, which is in signal communication with said second table for access to the latter such that each may generate said ultrasonic waveform signal by appropriately combining said combination sequence and said phase delays. In an embodiment, a method comprises: receiving a digital clock signal providing a determined number of clock pulses during a recording period; receiving, during the recording period, a plurality of binary digital signals, the plurality of binary digital signals defining, for each clock pulse of the determined number of clock pulses, a waveform state associated with the clock pulse; and generating a digital representation of a waveform having a duration based on the recording period and a profile based on the defined waveform states associated with the clock pulses of the determined number of clock pulses. In an embodiment, the generating the digital representation of the waveform comprises: representing the waveform as a series of bit sequences, each bit sequence of the series of bit sequences including a first plurality of bits representing a number of successive clock pulses in which the defined waveform maintains a current waveform state and a second plurality of bits corresponding to the plurality of binary digital signals defining the current waveform state. In an embodiment, the method includes storing the series of bit sequences. In an embodiment, the method comprises generating respective sets of the first plurality of bits of the series of bit sequences based on the received digital clock signal and the received plurality of binary digital signals. In an embodiment, each bit sequence of the series of bit sequences corresponds to a waveform period having a duration corresponding to number of successive clock pulses in which the defined waveform maintains the current waveform state. In an embodiment, the method comprises: determining when a boundary of a pair of adjacent waveform periods corresponds to a synchronous change of two or more signals of the plurality of binary signals; when it is determined that a boundary of a pair of adjacent waveform periods corresponds to a synchronous change of two or more signals of the plurality of binary signals, detecting one or more repetitions of the pair of adjacent waveform periods; and when one or more repetitions of the pair of adjacent waveform periods is detected, incrementing a repetition counter associated with the pair of adjacent waveforms periods. In an embodiment, when the repetition counter associated with the pair of adjacent waveform periods indicates one or more repetitions of the pair of waveform periods has been detected: the series of bit sequences includes a pair of bit sequences associated with the pair of adjacent waveform periods; and the digital representation of the waveform includes the repetition counter associated with the pair of adjacent waveform periods. In an embodiment, the series of bit sequences does not include additional bit sequences associated with repetitions of the pair of adjacent waveform periods. In an embodiment, the method comprises: receiving a binary signal defining the recording period, wherein the recording period starts at a start of a first state of the binary signal defining the recording period and ends at a start of a second state of the binary signal defining the recording period. In an embodiment, the method comprises: sending the digital representation of the waveform to an ultrasound generator. In an embodiment, each waveform state corresponds to an operating state of an ultrasound imaging apparatus.

In an embodiment a device comprises: an input configured to receive: a digital clock signal providing a determined number of clock pulses during a recording period; a plurality of binary digital signals, the plurality of binary digital signals defining, for each clock pulse of the determined number of clock pulses, a waveform state associated with the clock pulse; and circuitry coupled to the input and configured to generate a digital representation of a waveform having a duration based on the recording period and a profile based on the defined waveform states associated with the clock pulses of the determined number of clock pulses. In an embodiment, the circuitry is configured to represent the waveform as a series of bit sequences, each bit sequence of the series of bit sequences including a first plurality of bits representing a number of successive clock pulses in which the defined waveform maintains a current waveform state and a second plurality of bits corresponding to the plurality of binary digital signals defining the current waveform state. In an embodiment, the circuitry comprises a memory configured to store the series of bit sequences. In an embodiment, the circuitry comprises a counter and is configured to generate respective sets of the first plurality of bits of the series of bit sequences by counting numbers of successive clock pulses in which the defined waveform maintains current waveform states. In an embodiment, each bit sequence of the series of bit sequences corresponds to a waveform period having a duration corresponding to number of successive clock pulses in which the defined waveform maintains the current waveform state. In an embodiment, the circuitry is configured to: determine when a boundary of a pair of adjacent waveform periods corresponds to a synchronous change of two or more signals of the plurality of binary signals; when it is determined that a boundary of a pair of adjacent waveform periods corresponds to a synchronous change of two or more signals of the plurality of binary signals, detect one or more repetitions of the pair of adjacent waveform periods; and when one or more repetitions of the pair of adjacent waveform periods is detected, increment a repetition counter associated with the pair of adjacent waveforms periods. In an embodiment, when the repetition counter associated with the pair of adjacent waveform periods indicates one or more repetitions of the pair of waveform periods has been detected, the circuitry is configured to: associate a pair of bit sequences associated with the pair of adjacent waveform periods with the repetition counter. In an embodiment, the series of bit sequences does not include additional bit sequences associated with repetitions of the pair of adjacent waveform periods. In an embodiment, the input is configured to receive a binary signal defining the recording period. In an embodiment, the device includes a phase-shift controller configured to generate phase-shift control signals.

In an embodiment, a system comprises: a waveform representation generator configured to generate a digital representation of a waveform based on a digital clock signal providing a number of clock pulses during a recording period and a plurality of binary digital signals received during the recording period, the plurality of binary digital signals defining, for each clock pulse of the determined number of clock pulses, a waveform state associated with the clock pulse, the digital representation of the waveform having a duration based on the recording period and a profile based on the defined waveform states associated with the clock pulses of the number of clock pulses; a phase-shift controller configured to generate phase-shift control signals; and a plurality of transducers configured to receive the digital representation of the waveform and respective phase shift control signals and to generate ultrasonic waveforms based on the received digital representation and respective phase shift control signals. In an embodiment, the waveform representation generator is configured to represent the waveform as a series of bit sequences, each bit sequence of the series of bit sequences including a first plurality of bits representing a number of successive clock pulses in which the defined waveform maintains a current waveform state and a second plurality of bits corresponding to the plurality of binary digital signals defining the current waveform state. In an embodiment, the waveform representation generator comprises a counter and is configured to generate respective sets of the first plurality of bits of the series of bit sequences by counting numbers of successive clock pulses in which the defined waveform maintains current waveform states. In an embodiment, each bit sequence of the series of bit sequences corresponds to a waveform period having a duration corresponding to number of successive clock pulses in which the defined waveform maintains the current waveform state. In an embodiment, the waveform representation generator is configured to: determine when a boundary of a pair of adjacent waveform periods corresponds to a synchronous change of two or more signals of the plurality of binary signals; when it is determined that a boundary of a pair of adjacent waveform periods corresponds to a synchronous change of two or more signals of the plurality of binary signals, detect one or more repetitions of the pair of adjacent waveform periods; and when one or more repetitions of the pair of adjacent waveform periods is detected, increment a repetition counter associated with the pair of adjacent waveforms periods. In an embodiment, when the repetition counter associated with the pair of adjacent waveform periods indicates one or more repetitions of the pair of waveform periods has been detected, the waveform representation generator is configured to: associate a pair of bit sequences associated with the pair of adjacent waveform periods with the repetition counter. In an embodiment, the waveform representation generator is configured to receive a binary signal defining the recording period.

DETAILED DESCRIPTION

Figure 1:
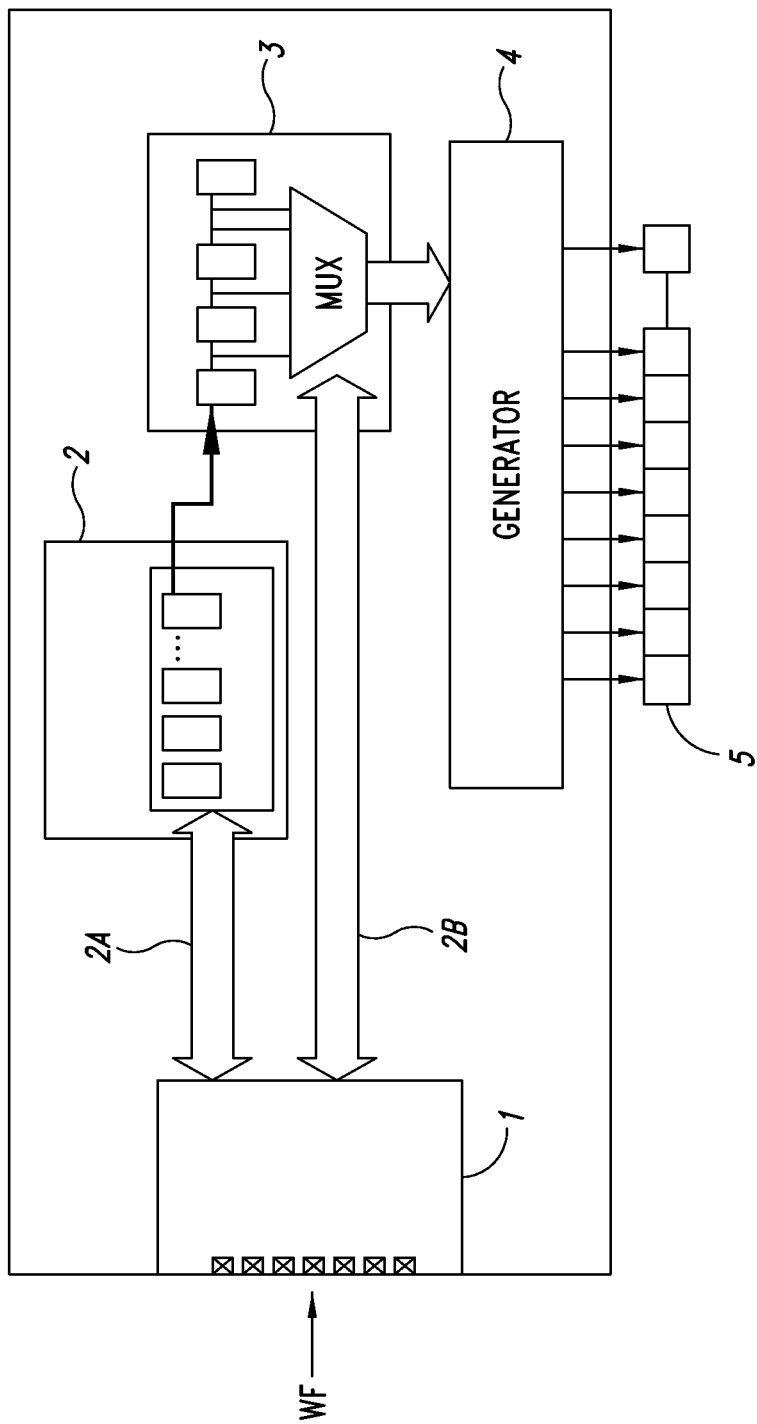
FIG. 1 shows a block diagram of an integrated circuit that is used in a prior art imaging system.

In the following description, certain details are set forth in order to provide a thorough understanding of various embodiments of devices, methods and articles. However, one of skill in the art will understand that other embodiments may be practiced without these details. In other instances, well-known structures and methods associated with, for example, signal processing devices, interfaces, etc., have not been shown or described in detail in some figures to avoid unnecessarily obscuring descriptions of the embodiments.

Unless the context requires otherwise, throughout the specification and claims which follow, the word "comprise" and variations thereof, such as "comprising," and "comprises," are to be construed in an open, inclusive sense, that is, as "including, but not limited to."

Reference throughout this specification to "one embodiment," "a first embodiment," "an embodiment," etc., means that a particular feature, structure or characteristic described in connection with the embodiment is included in at least one embodiment. Thus, the appearances of the phrases "in one embodiment," or "in an embodiment" in various places throughout this specification are not necessarily referring to the same embodiment, or to all embodiments. Furthermore, the particular features, structures, or characteristics may be combined in any suitable manner in one or more embodiments to obtain further embodiments.

The headings are provided for convenience only, and do not interpret the scope or meaning of this disclosure.

The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn are not necessarily intended to convey any information regarding the actual shape of particular elements, and have been selected solely for ease of recognition in the drawings.

Although this is not expressly shown, the individual features described with reference to example embodiments shall be intended as auxiliary and/or interchangeable with other features, as described with reference to other embodiments.

The present disclosure relates to a method and a device for setting a waveform signal in an ultrasound imaging apparatus.

Figure 2:
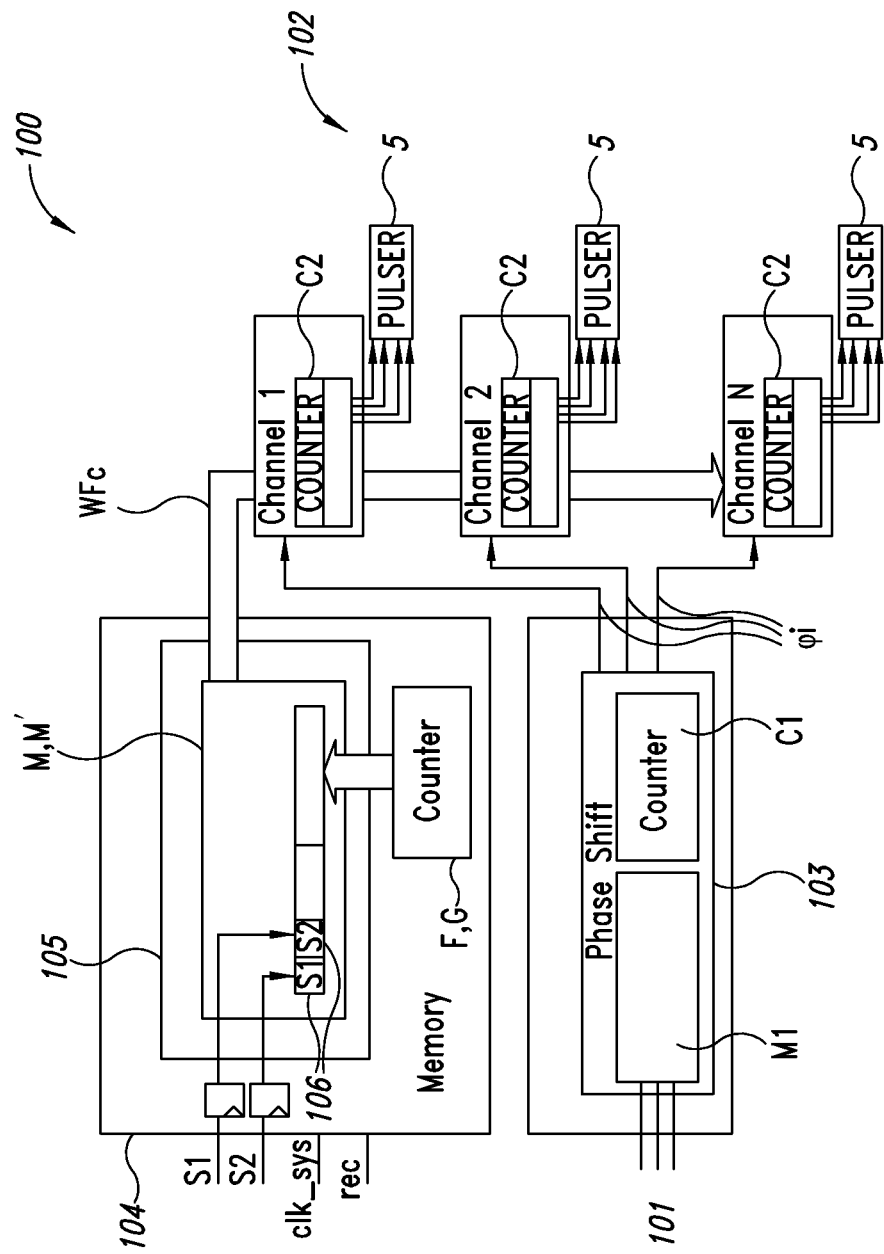
FIG. 2 shows a block diagram of an embodiment of an integrated circuit.

The accompanying figures show the method of setting a waveform signal WF (or acoustic signal) in the apparatus, with FIG. 2 showing a possible device adapted for implementation of such method in the ultrasound imaging apparatus.

Figure 3:
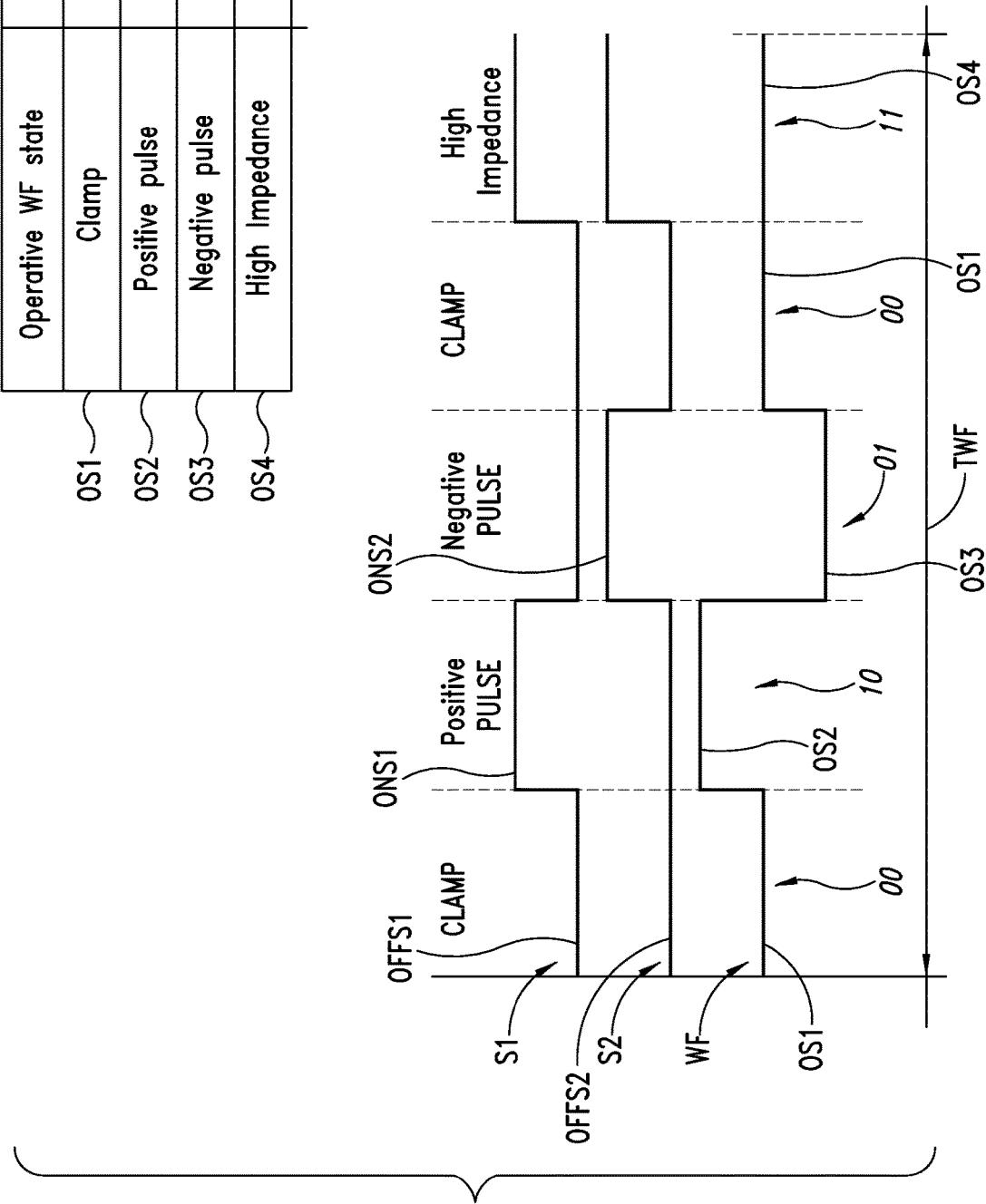
FIG. 3 shows a possible association of the operating states of the acoustic signals with the recorded signals.

Referring now to FIG. 3, WF designates the acoustic signal having a determined profile (or time curve) (e.g., a predetermined profile) and a set duration $T_{WF}$ (i.e., a preset duration from the start time to the end time, equal to $T_{WF}$).

The signal WF represents the acoustic signal to be emitted by the ultrasound imaging apparatus (FIG. 2).

Particularly, the profile of the signal WF defines a plurality of operating or waveform states OS1, . . . , OS4, which represent a particular operating condition of the ultrasound imaging apparatus.

For example, as shown in this FIG. 3, according to the present disclosure, the operating state OS1 designates a clamp state (grounded transducer 5) of the signal WF, the operating state OS2 designates a positive (or high) pulse state, the operating state OS3 designates the negative (or low) pulse state and the operating state OS4 designates the high impedance state (the state in which the transducer 5 is not controlled and is in an idle state).

Figure 4:
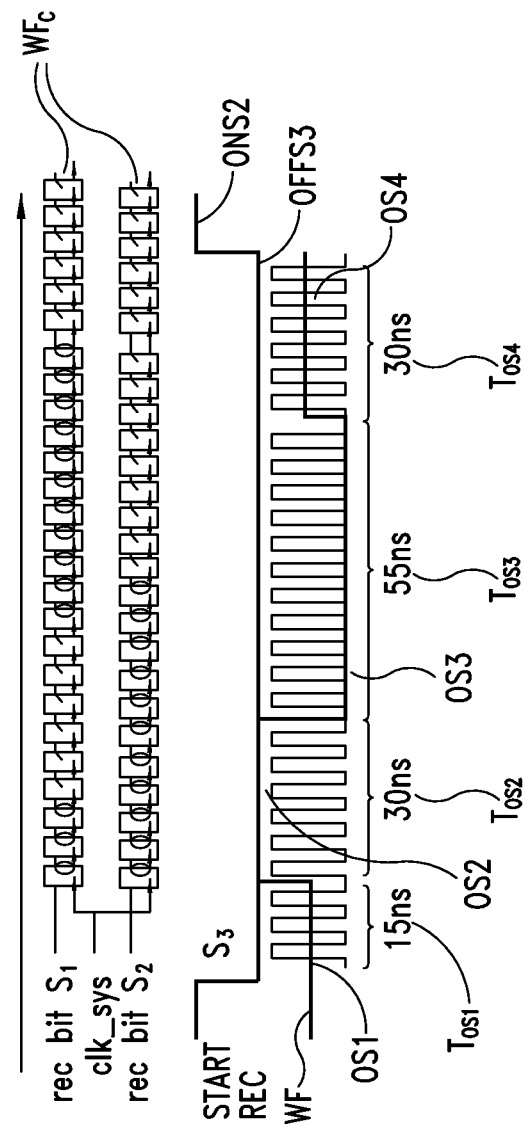
FIG. 4 shows a possible recording signal combination sequence according to an embodiment.

For instance, in the table of FIG. 4, four operating states of the signal WF are indicated, but there may presumably be acoustic signals with more complex profiles, for example, comprising more than the above-mentioned four operating states.

As shown in this FIG. 3 and according to the present disclosure, at least one first and one second binary digital signals S1, S2 are provided in the method of setting a waveform signal in the ultrasound imaging apparatus, each of said signals defining two signal operating states ONs1, OFFs1 and ONs2, OFFs2.

Particularly, the two operating states ONs1, OFFs1 and ONs2, OFFs2 of the respective digital signals S1, S2 represent a high state (ONs1, ONs2) and a low state (OFFs1, OFFs2) that may be assumed by each signal S1, S2 respectively.

These digital signals S1, S2 may be represented by one bit each (FIG. 4).

Each operating state of the plurality of operating or waveform states OS1, . . . , OS4 is associated with a combination of said two operating states (ONs1, OFFs1 and ONs2, OFFs2) of the at least one first signal S1 and second signal S2.

In this FIG. 3, concerning the case in which the signal WF has a profile with four operating states, it can be noted that:
the operating state OS1 is associated with the low-state combination of the two signals S1, S2, i.e., OS1 equal to 00;
the operating state OS2 is associated with the high-state combination of the signal S2, i.e., OS2 equal to 10;
the operating state OS3 is associated with the low-state combination of the signal S2, i.e., OS3 equal to 01; and
the operating state OS4 is associated with the high-state combination of the signals S1, S2, i.e., OS1 equal to 11;

Referring now to FIG. 4, the imaging apparatus is provided with a digital clock signal clk_sys that defines a number of clock pulses P having a preset period Pclk_sys and, optionally, a further digital signal S3, which represents the controls signal for the start and end of the associating operations.

It shall be noted that the digital signal S3 also defines two operating states ONs3, OFFs3.

This digital signal S3 may be represented by a single bit.

Particularly, the above-described association allows storage of a combination sequence $WF_C$ of the two operating states ONs1, OFFs1 and ONs2, OFFs2 of the signals S1, S2, thereby generating a digital waveform coded signal.

This combination sequence $WF_C$ has a duration equal to the preset duration $T_{WF}$ of the digital waveform signal WF and represents the profile to be sent to the ultrasound imaging apparatus.

Thus, still referring to FIG. 4, it can be noted that the signal WF is submitted to a sampling operation by association of each operating state of the plurality of operating states OS1, . . . , OS4 of the signal WF with a combination of said two operating states ONs1, OFFs1 and ONs2, OFFs2 of the signals S1 and S2.

Therefore the combination sequence $WF_C$ comprises a number of combinations of the two operating states ONs1, OFFs1 and ONs2, OFFs2 of the signals S1 and S2 that is equal to the number of clock pulses P of the clock signal clk_sys in the preset duration $T_{WF}$ of the signal WF.

It shall be noted that each of the operating states OS1, . . . , OS4 of the waveform signal WF has its own duration $T_{OS1}, \ldots, T_{OS4}$.

Therefore the combination sequence $WF_C$ comprises a number of combinations of the two operating states ONs1, OFFs1; ONs2, OFFs2 of the signals S1 and S2 that is preferably equal to the number of clock pulses P in the duration $T_{OS1}, \ldots, T_{OS4}$ of each of the operating states OS1, . . . , OS4 of the signal WF.

In other words, and still referring to FIG. 4, it can be noted, for example, that the operating state OS1 of the signal WF has a duration $T_{OS1}$ that is longer than the period of the clock signal clk_sys, and hence the association is performed, within its duration $T_{OS1}$, as many times as there are clock pulses in such duration $T_{OS1}$.

For example, assuming a duration $T_{WF}$ of 130 nsec and a clock signal clk_sys having a frequency of 200 MHz (a period of Pclk_sys of 5 nsec) and assuming that $T_{OS1}$ is equal to 15 nsec, then the signal WF will have a profile that remains in the operating state OS1 (or clamp state) for three clock pulses (with $T_{OS1}/P_{clk}$=15 nsec/5 nsec=3 clock pulses) and hence the combination sequence has six memory elements (as three elements are required for the signal S1 and three elements are required for the signal S2) for such operating state OS1 to be stored.

The same applies to the other operating states exemplified in FIG. 4.

Therefore, as the combination sequence $WF_C$ has to code four operating states OS1, . . . , OS4 of the signal WF, it will comprise 130/5=26 memory elements (or flip-flops) for each signal S1 and S2, i.e., a total of 52 memory elements (see the device of FIG. 2) for storing the combination sequence.

In an embodiment, the step of associating the combination sequence or storing it in the memory devices starts at the start of the first operating state of the signal S3 and ends at the same time as the start of the second operating state of such third signal S3.

In other words, the signal S3 is used as a recording switch.

For example, its high operating state (value 1) is associated with the step of stopping association, and its low operating state (value 0) is associated with the step of starting association.

Figure 5:
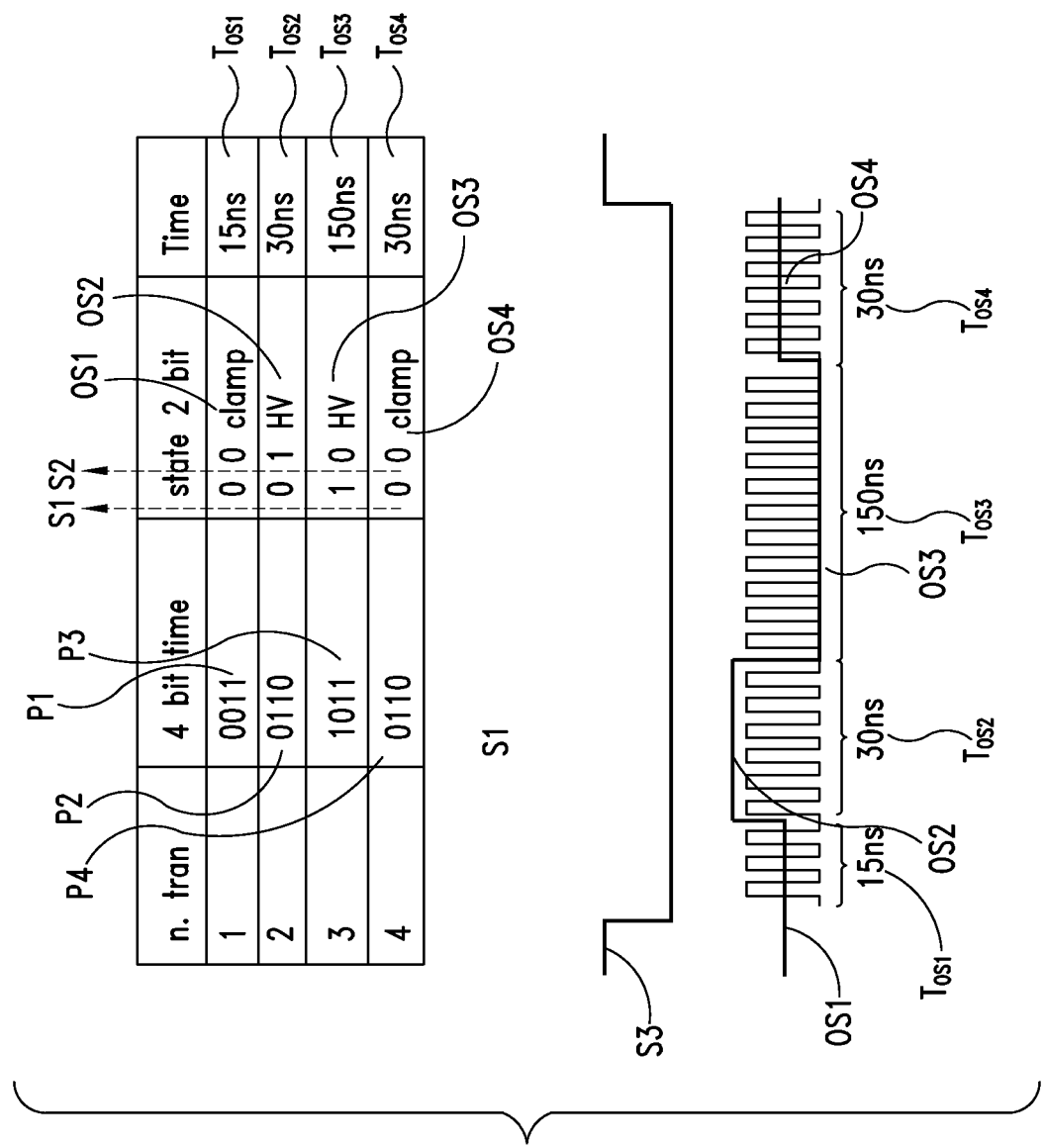
FIG. 5 shows a possible form of compression of the recorded signal combination sequence of FIG. 4, according an embodiment.

Referring now to FIG. 5, to improve the associating step and facilitate a more efficient compression of the combination sequence, thereby facilitating the use of a smaller number of memory devices, the present disclosure provides the implementation of a method that allows assessment, during the period $T_{OS1}, \ldots, T_{OS4}$ of each of the operating states OS1, . . . , OS4, of the time during which each of said operating states OS1, . . . , OS4 of the signal WF is constant at that value, and the corresponding (high or low) values of the signals S1, S2.

Such assessment is based on the number of clock pulses P that the clock signal clk_sys has (or are included) during the period $T_{OS1}, \ldots, T_{OS4}$ of each of the operating states, i.e., on the number of clock pulses within one period $T_{OS1}, \ldots, T_{OS4}$.

Thus a smaller memory area will be required for storage of the information needed to compose the combination sequence that is recorded in an appropriate memory table.

In an embodiment, the method comprises determination of a value representative of the number of clock pulses P1, . . . , P4 within the duration $T_{OS1}, \ldots, T_{OS4}$ of each operating state of the plurality of operating states OS1, . . . , OS4 of the signal WF and association of such value representative of the number of clock pulses with each operating step OS1, . . . , OS4 of said digital waveform signal WF.

The combination sequence comprises a number of the operating states ONs1, OFFs1; ONs2, OFFs2 of the signals S1 and S2 that is preferably equal to the number of clock pulses P1, . . . , P4 for each operating state of said plurality of operating states OS1, . . . , OS4 of the signal WF.

This number of clock pulses P1, . . . , P4 may be represented, for example, by four bits each.

In other words, still referring to the table of such FIG. 5, it can be noted that, for the transition number T1 (operating state OS1 and duration $T_{OS1}$), the number of clock pulses P1 within the duration of the operating state OS1 of the signal WF is determined according to the clock period ($T_{OS1}/P_{clk\_sys}$=P1) and the combination sequence comprises $WF_C$ such number of clock pulses P1 for the corresponding operating state of the signals S1, S2 (S1=S2=clamp) in such operating state OS1 of the signal WF.

With the above numbers, P1 will be equal to three clock pulses and the operating state of the signals S1, S2 is 00, such that the combination sequence comprises four bits representing the number of clock pulses P1 and two additional bits representing the respective operating states of the signals S1, S2, thus amounting to six bits.

Similar results are achieved with the other transitions T2, . . . , T4.

With this operation, the number of flip-flops needed for storing the profile of the acoustic signal WF is considerably decreased.

Storage of a waveform like that of FIG. 5 may be accomplished using two bits for the state and four additional bits for the state permanence time, for each state change (4), hence a total of 24 bits.

Figure 6A:
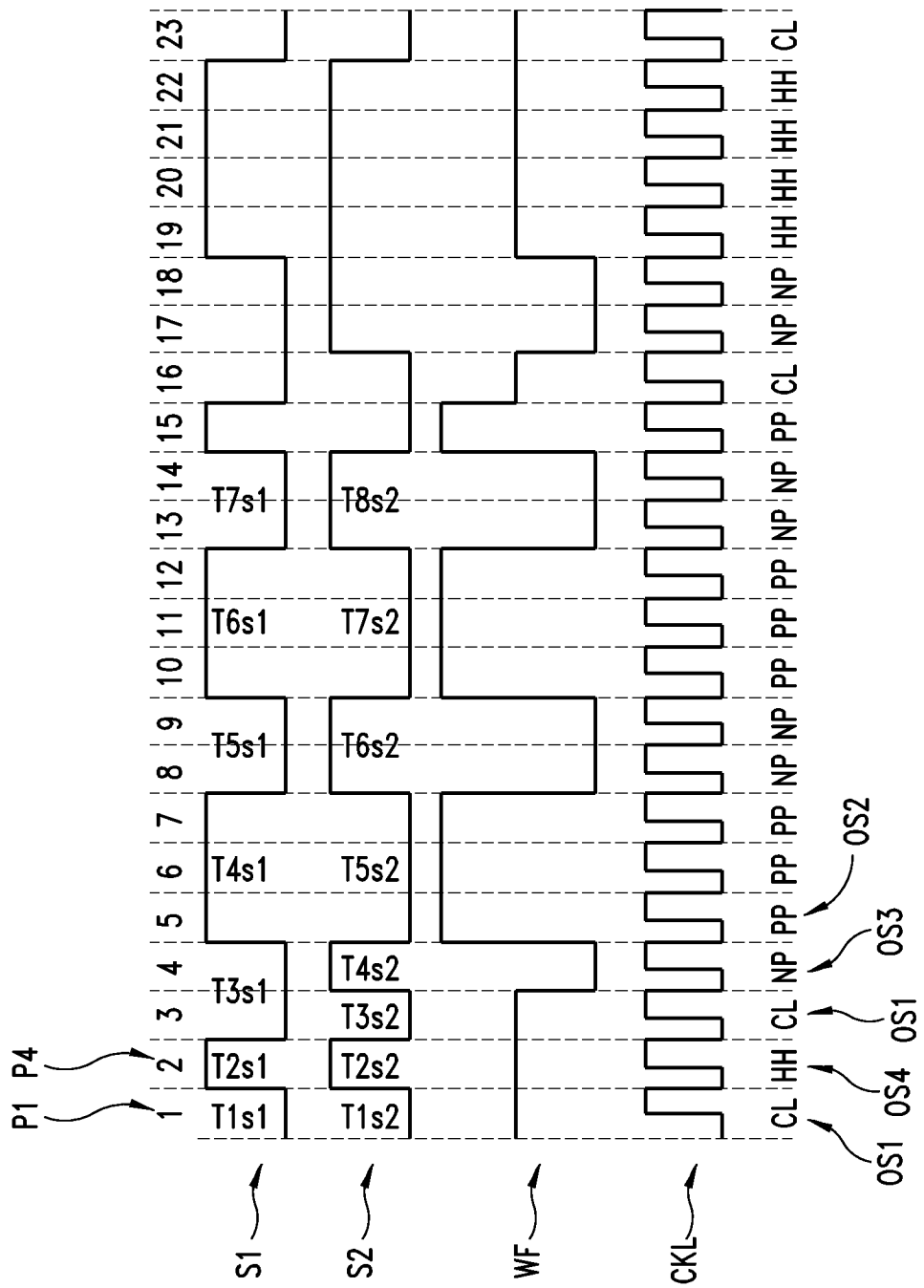
FIGS. 6A and 6B show a further possible form of compression of the recorded signal combination sequence of FIG. 4, according to an embodiment.

Storage of a more complex waveform like that of FIG. 6A may be accomplished using two bits for the state and three additional bits for the state permanence time, for each state change (13), hence a total of 65 bits.

This may considerably reduce also the configuration time, that will be: $T_{conf}$=23×5 ns=115 ns.

Indeed, since the waveform is configured in the device by recording, the time is dependent on, namely equal to, the duration of the waveform itself, and is independent of any communication protocol time.

Of course, the shorter the waveform to be stored, the shorter the configuration time, which will increase the efficiency of the system. In an embodiment, the setup of a simple waveform will not require many communication operations as required by an interface protocol, and many configuration bits, but only as much time and as many bits as necessary.

Figure 6B:
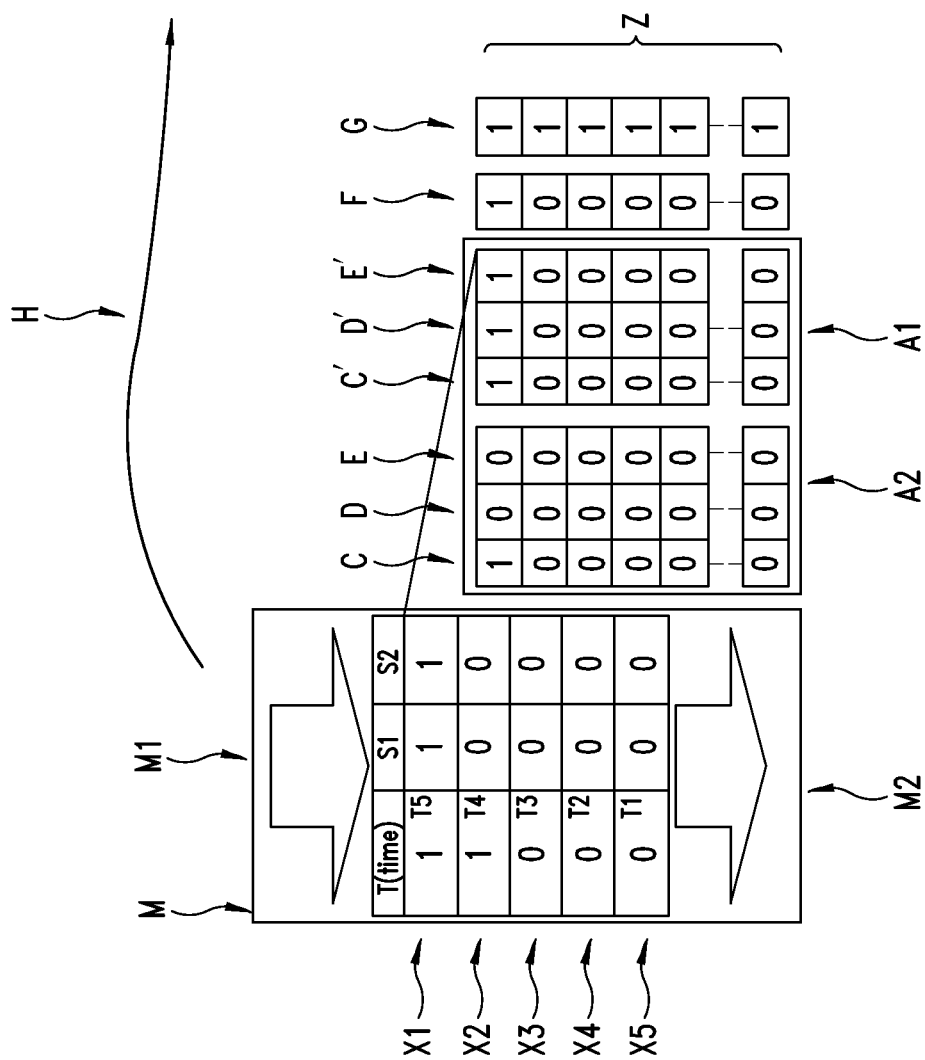

Referring now to FIGS. 6A and 6B, in order to improve the associating step and facilitate a more efficient compression, thereby facilitating the use of a smaller number of memory devices, the present disclosure provides the detection of repetitions of two or more adjacent sequences, in addition to assessment of the duration $T_{OS1}, \ldots, T_{OS4}$ of each of the operating states OS1, . . . , OS4 of the signal WF in which the latter is constant, and the corresponding level of the signals S1, S2.

These sequences equally consist of two combinations of the operating states ONs1, OFFs1 of the signal S1 and the operating states ONs2, OFFs2 of the signal S2, separated by a single transition of S1 or a single transition of S2, or simultaneous transitions of both signals. The repetition will be confirmed when the sequences are described by identical values of OS and Tos. In this case, a single repetition will be stored, with a number R indicative of its recurrence.

It will be understood that, since a single repetition of such combination is stored for both the signal S1 and the signal S2, the combination sequence recorded in a memory table occupies a smaller area than in the method as described with reference to FIG. 5.

Therefore, the above method allows detection of the repetition of adjacent pairs of combinations of the signals S1 and S2, particularly when the variation of S1 and S2 is synchronous.

FIG. 6A shows the situation in which, for each operating state OS1, . . . , OS4 of the signal WF, an assessment is performed of the rate of repetition R of sequences containing two combinations of the operating states ONs1, OFFs1 of the signal S1 and the operating states ONs2, OFFs2 of the signal S2, where the transition from the first combination to the second combination only occurs by synchronous transitions of S1 and/or S2.

It can be noted, for example, that the adjacent periods T4$s$1 and T5$s$1 of the signal S1, characterized by a state permanence R of three for the operating state ONs1 and a state permanence R of two for the operating state OFFs1 respectively, are repeated in their characterization in the periods T6$s$1 and T7$s$1 of the same signal S1.

This repetition occurs as times and operating states for the signal S2 in the adjacent periods T5$s$2 and T6$s$2 with a state permanence R of three, repeated at T7$s$2 and T8$s$2 with a state permanence R of two.

Therefore, since the two adjacent operating states T4$s$1-T5$s$1 of the signal S1 have a state permanence value R of three and two respectively and are repeated in the operating states T6$s$1-T7$s$1 with the same state permanence values R, the present disclosure provides storage of a single repetition (e.g., the one for the two adjacent operating states T4$s$1-T5$s$1) and of their state permanence value R (three and two respectively).

Identical conclusions apply to the two adjacent operating states of the signal S2.

Referring now to FIG. 6B, in order to store a single repetition and the repetition rate when even two or more adjacent operating states OS1, . . . , OS4 of the signal S1 and the signal S2 are repeated, the present method uses a table M, having five lines x1, . . . , x5 and m columns, which acts as a buffer.

This buffer M pre-stores the level of the operating state of the signals S1, S2 and their state permanence value R (from 1 to 5), i.e., the input data, designated as M1 in this FIG. 6B, with the M2 data at the output, the latter data not being considered in this first implementation.

In this table M, which acts as a preliminary buffer, the method checks for equivalence of the operating states of the signals S1, S2.

For this purpose, when two lines of the table M are full, the same content is stored as a double array A1, A2 of three columns and z lines (as shown in the Figure by dashed lines).

It shall be noted that the array A1 has a first column C designating the first instant of time and the next columns D, E designating the values of the first operating states OS of the signal S1 and the signal S2, whereas the array A2 has a first column C' designating the second instant of time and the next columns D', E' designating the values of the second operating states OS of the signal S1 and the signal S2.

The method provides control of the data stored in such arrays A1, A2 as soon as the first three lines X5, X4 and X3 of the matrix M are filled, said lines being the last lines that have been filled with the data M1.

If equivalence is confirmed, a memory flag F is updated, whereby the next line in the table M is prevented from being increased, such that the information of the next operating levels will replace it and a relative repetition index G will be increased.

If equivalence is not confirmed, as shown by arrow H, then the memory flag F will be increased and the next pulse in the next empty line of table M will be stored.

Figure 7A:
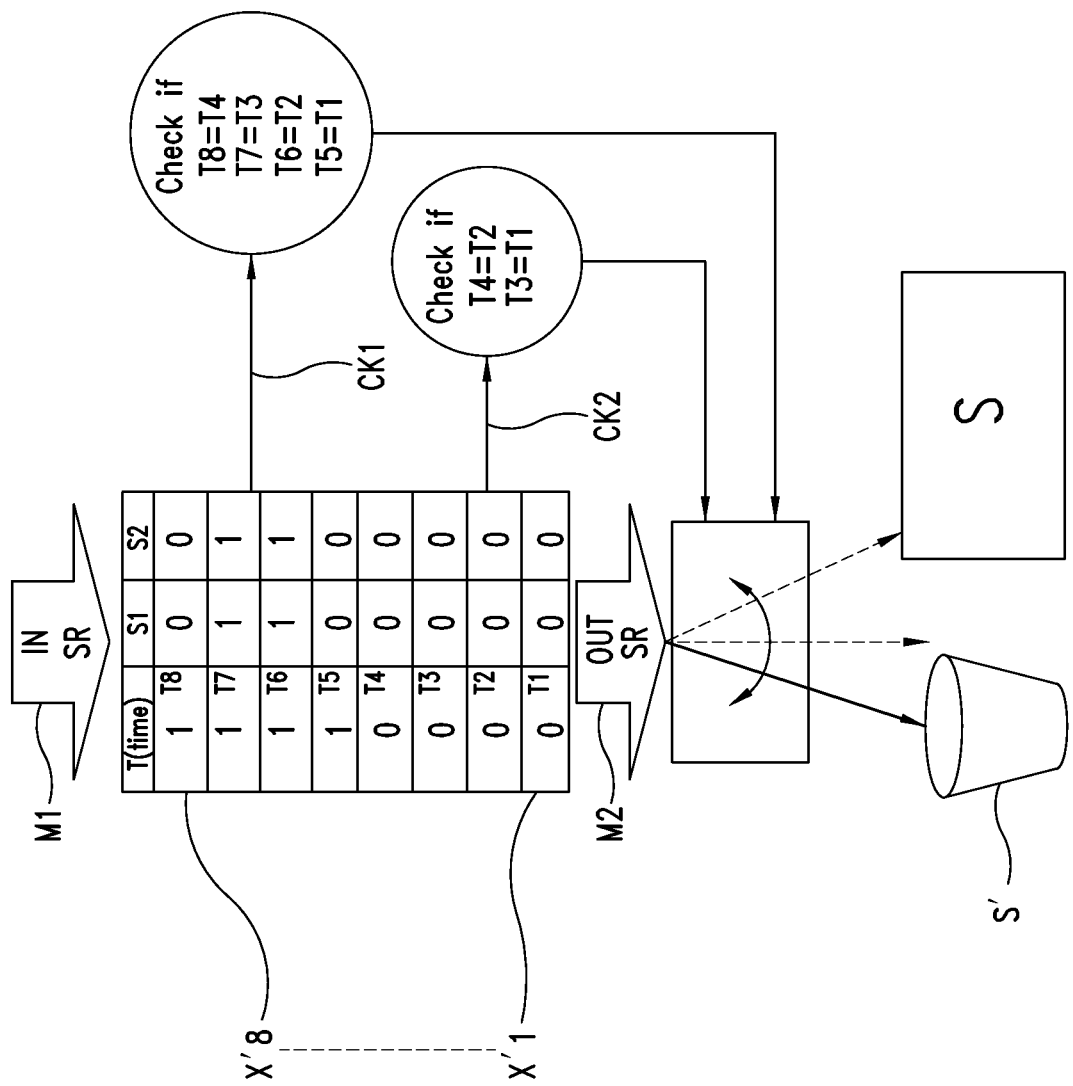
FIGS. 7A and 7B show a further possible form of compression of the recorded signal combination sequence of FIGS. 6A and 6B according to an embodiment.
Figure 7B:
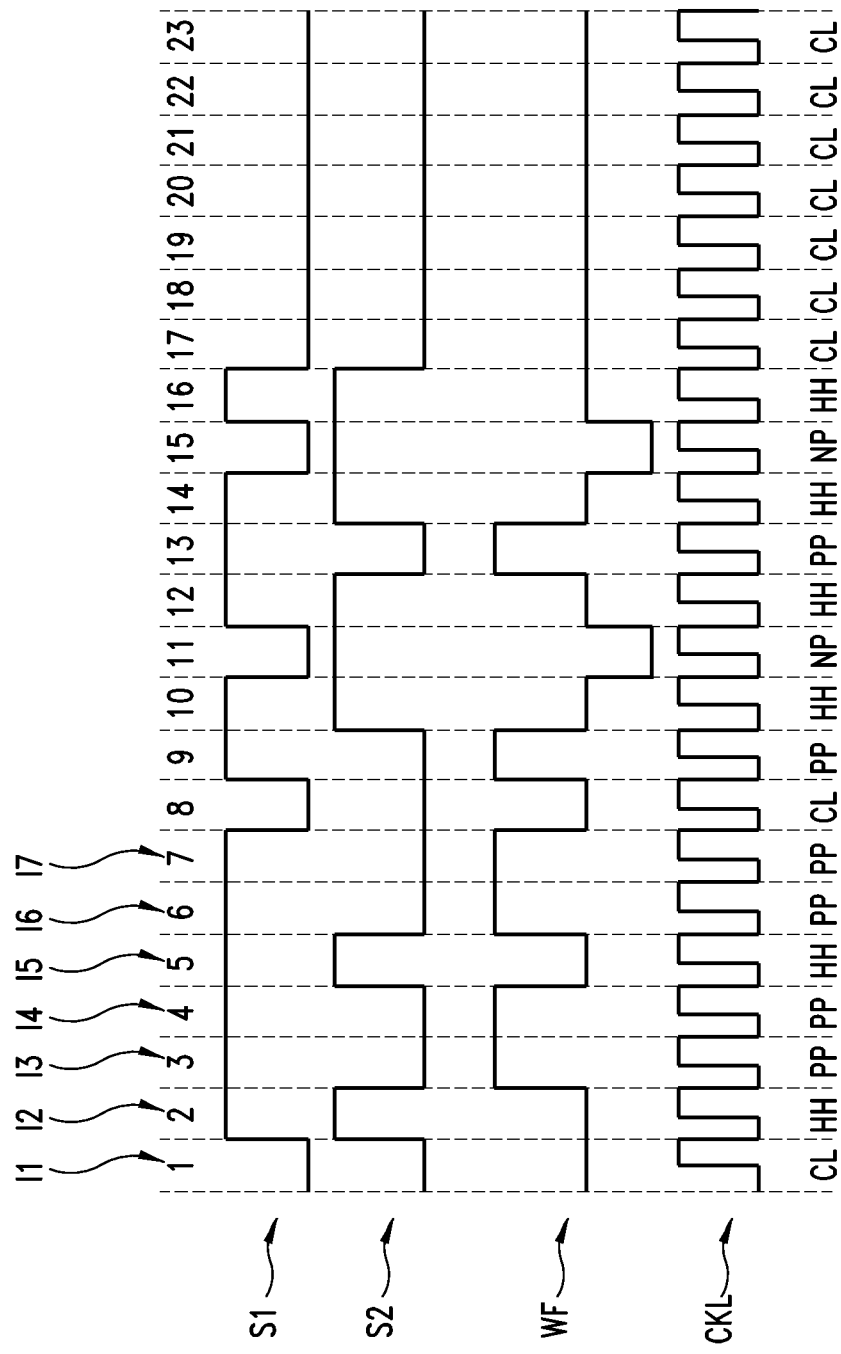

FIGS. 7A and 7B show a second implementation in which the number of transitions in the equivalence check is increased, to allow detection of equivalences between adjacent sequences also consisting of more than two combinations of the operating states ONs1, OFFs1 of the signal S1 and the operating states ONs2, OFFs2 of the signal S2 and hence also operating in cases of non-synchronous transitions between the two signals S1 and S2.

Thus, also referring to FIG. 7A, the combination sequence $WF_C$ of the present method uses a table M' having eight lines (X'1 to X'8) and m columns, which acts as a buffer that pre-stores the level of the operating state of the signals S1, S2 and their state permanence R.

The buffer M' is filled from the line 8 and emptied from the line 1.

The content of the line 1 may be discarded or stored in a memory, depending on the result of the equivalence checks.

When the line 1 is filled, two controls CK1 and CK2 are made: the first T1=T3 and T2=T4 at low priority and the second T1=T4 T2=T5 T3=T6 and T4=T8 at high priority.

If the first check CK1 is successful, then the lines T1 and T2 will be discarded (as shown by S1 in FIG. 7) as the values in the buffer M1 move from the storage vector T8 to T1, whereas the values of the storage vectors T3 and T4 are shifted out of the buffer and stored in the memory, where they are tagged with a value that designates the number of detected repetitions.

If the second check CK2 is confirmed, the contents of T1 T2 T3 T4 will be discarded and only the contents of lines T5 T6 T7 T8 will be stored, with a value designating the number of repetitions associated therewith.

If both checks CK1, CK2 coincide, the check at high propriety (here the second check CK2) will win.

Alternatively, the size of the buffer system M' may vary as needed.

For example, a further check may be added, to be performed at least on two contiguous states, such as T1=T2 and, in this case, if the check is confirmed then only the value stored by the vector T2 will be retained, with a non-zero repetition value.

The buffer size may be increased to further increase the number of events in an equivalence interval.

Referring now to the waveform of FIG. 7B, it can be noted that both the operating states of the signal S1 and those of the signal S2 in the interval containing the instants I2, I3, I4 are repeated with their values and durations in the interval containing the instants I5, I6, I7.

The repetition also occurs between the interval containing the instants I9, I10, I11, I12 and the interval containing the instants I13, I14, I15, I16.

The first repetition I2, I3, I4 and I5, I6, I7 for the signals S1 and S2 is detected during the check CK1 as two successive periods T are repeated.

The second repetition I9, I10, I11, I12 and I13, I14, I15, I16 is detected during the CK2, as four successive periods T are repeated.

FIG. 2 shows a device 100 for setting a waveform signal WF in an ultrasound imaging apparatus.

The ultrasound imaging apparatus comprises a plurality of transducers 5, each being configured to generate an ultrasonic waveform signal using known techniques, that will not be described herein.

The device 100 for setting a waveform signal WF comprises a phase-shift unit 103, which is operatively configured to receive the data concerning the delays to be associated to each output channel.

Such phase shift unit 103 is in signal communication with each transducer 5 to send it a respective phase delay $\varphi_i$.

The device 100 comprises a storage unit 104, as illustrated, a memory, which is configured to receive at least the digital clock signal clk_sys (i.e., the signal defining the number of clock pulses of predetermined period) and at least one first and one second digital signals S1, S2 whose combination leads to the combination sequence $WF_C$ as described above with reference to FIGS. 3 to 8.

Optionally, the storage unit 104 also receives the signal S3, the signal that starts/stops the associating step.

The storage unit 104 is in signal communication with each transducer 5 of the plurality of transducers 102 to send the combination sequence $WF_C$.

Particularly, the storage unit 104 comprises:
compression means 105 configured to sample the changes of the operating states of the combination sequence $WF_C$ according to the values of the operating states of the signals S1, S2 (which may be stored in flip-flops 106);
a first memory table M, M' configured to store the changes of the operating states of the sequence of combination sequence $WF_C$;
a first counter F, G to count the time between two continuous events of said sequence of combination sequence $WF_C$.

The phase shift unit 103 comprises a second memory table M1 configured to store phase delays for each transducer 5 of said plurality of transducers 102 and a counter C1 to count the occurrences of phase delays exceeding the value set in the delay counter. As illustrated, the phase shift unit 103 comprises an input 101 configured to receive, for example, phase delay information.

It shall be noted that each transducer 102 may comprise its own counter C2, which is in signal communication with the second table M1 for access to the latter such that each transducer may generate the acoustic signal WF by appropriately combining the combination sequence $WF_C$ and the phase delays $\varphi_i$.

Those skilled in the art will obviously appreciate that a number of changes and variants as described above may be made to fulfill particular requirements, without departure from the scope of the disclosure.

Some embodiments may take the form of or include computer program products. For example, according to one embodiment there is provided a computer readable medium including a computer program adapted to perform one or more of the methods or functions described above. The medium may be a physical storage medium such as for example a Read Only Memory (ROM) chip, or a disk such as a Digital Versatile Disk (DVD-ROM), Compact Disk (CD-ROM), a hard disk, a memory, a network, or a portable media article to be read by an appropriate drive or via an appropriate connection, including as encoded in one or more barcodes or other related codes stored on one or more such computer-readable mediums and being readable by an appropriate reader device.

Furthermore, in some embodiments, some of the systems and/or modules and/or circuits and/or blocks may be implemented or provided in other manners, such as at least partially in firmware and/or hardware, including, but not limited to, one or more application-specific integrated circuits (ASICs), digital signal processors, discrete circuitry, logic gates, standard integrated circuits, controllers (e.g., by executing appropriate instructions, and including microcontrollers and/or embedded controllers), field-programmable gate arrays (FPGAs), counters, complex programmable logic devices (CPLDs), etc., as well as devices that employ RFID technology, and various combinations thereof.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method, comprising:
receiving a digital clock signal providing a determined number of clock pulses during a recording period;
receiving, during the recording period, a plurality of binary digital signals, the plurality of binary digital signals defining, for each clock pulse of the determined number of clock pulses, a waveform state associated with the clock pulse; and
generating a digital representation of a waveform having a duration based on the recording period and a profile based on the defined waveform states associated with the clock pulses of the determined number of clock pulses, the digital representation of the waveform including a series of bit sequences, each bit sequence of the series of bit sequences including a first plurality of bits representing a number of successive clock pulses in which the respective defined waveform maintains a current waveform state and a second plurality of bits corresponding to the plurality of binary digital signals defining the current waveform state.

2. The method of claim 1, comprising:
storing the series of bit sequences.

3. The method of claim 1, comprising generating respective sets of the first plurality of bits of the series of bit sequences based on the received digital clock signal and the received plurality of binary digital signals.

4. The method of claim 1 wherein each bit sequence of the series of bit sequences corresponds to a waveform period having a duration corresponding to the number of successive clock pulses in which the defined waveform maintains the current waveform state.

5. The method of claim 1, comprising:
determining when a boundary of a pair of adjacent waveform periods corresponds to a synchronous change of two or more signals of the plurality of binary signals;
when it is determined that a boundary of a pair of adjacent waveform periods corresponds to a synchronous change of two or more signals of the plurality of binary signals, detecting one or more repetitions of the pair of adjacent waveform periods; and
when one or more repetitions of the pair of adjacent waveform periods is detected, incrementing a repetition counter associated with the pair of adjacent waveforms periods.

6. The method of claim 5 wherein when the repetition counter associated with the pair of adjacent waveform periods indicates one or more repetitions of the pair of waveform periods has been detected:
the series of bit sequences includes a pair of bit sequences associated with the pair of adjacent waveform periods; and
the digital representation of the waveform includes the repetition counter associated with the pair of adjacent waveform periods.

7. The method of claim 6 wherein the series of bit sequences does not include additional bit sequences associated with repetitions of the pair of adjacent waveform periods.

8. The method of claim 1, comprising:
receiving a binary signal defining the recording period, wherein the recording period starts at a start of a first state of the binary signal defining the recording period and ends at a start of a second state of the binary signal defining the recording period.

9. The method of claim 1, comprising:
sending the digital representation of the waveform to an ultrasound generator.

10. The method of claim 1 wherein each waveform state corresponds to an operating state of an ultrasound imaging apparatus.

11. A device, comprising:
a memory, which, in operation, receives:
a digital clock signal providing a determined number of clock pulses during a recording period;
a plurality of binary digital signals, the plurality of binary digital signals defining, for each clock pulse of the determined number of clock pulses, a waveform state associated with the clock pulse; and
circuitry coupled to the memory, and which, in operation, generates a digital representation of a waveform having a duration based on the recording period and a profile based on the defined waveform states associated with the clock pulses of the determined number of clock pulses, the digital representation including a series of bit sequences, each bit sequence of the series of bit sequences including a first plurality of bits representing a number of successive clock pulses in which the respective defined waveform maintains a current waveform state and a second plurality of bits corresponding to the plurality of binary digital signals defining the current waveform state.

12. The device of claim 11 wherein the circuitry comprises a second memory configured to store the series of bit sequences.

13. The device of claim 11 wherein the circuitry comprises a counter and is configured to generate respective sets of the first plurality of bits of the series of bit sequences by counting numbers of successive clock pulses in which the defined waveform maintains current waveform states.

14. The device of claim 11 wherein each bit sequence of the series of bit sequences corresponds to a waveform period having a duration corresponding to the number of successive clock pulses in which the defined waveform maintains the current waveform state.

15. The device of claim 11 wherein the circuitry, in operation:
determines when a boundary of a pair of adjacent waveform periods corresponds to a synchronous change of two or more signals of the plurality of binary signals;
when it is determined that a boundary of a pair of adjacent waveform periods corresponds to a synchronous change of two or more signals of the plurality of binary signals, detects one or more repetitions of the pair of adjacent waveform periods; and
when one or more repetitions of the pair of adjacent waveform periods is detected, increments a repetition counter associated with the pair of adjacent waveforms periods.

16. The device of claim 15 wherein when the repetition counter associated with the pair of adjacent waveform periods indicates one or more repetitions of the pair of waveform periods has been detected, the circuitry is configured to:
associate a pair of bit sequences associated with the pair of adjacent waveform periods with the repetition counter.

17. The device of claim 16 wherein the series of bit sequences does not include additional bit sequences associated with repetitions of the pair of adjacent waveform periods.

18. The device of claim 11 wherein the memory is configured to receive a binary signal defining the recording period.

19. The device of claim 11, comprising:
a phase-shift controller configured to generate phase-shift control signals.

20. A system, comprising:
a waveform representation generator configured to generate a digital representation of a waveform based on a digital clock signal providing a number of clock pulses during a recording period and a plurality of binary digital signals received during the recording period, the plurality of binary digital signals defining, for each clock pulse of the determined number of clock pulses, a waveform state associated with the clock pulse, the digital representation of the waveform having a duration based on the recording period and a profile based on the defined waveform states associated with the clock pulses of the number of clock pulses, the digital representation including a series of bit sequences, each bit sequence of the series of bit sequences including a first plurality of bits representing a number of successive clock pulses in which the respective defined waveform maintains a current waveform state and a second plurality of bits corresponding to the plurality of binary digital signals defining the current waveform state;
a phase-shift controller configured to generate phase-shift control signals; and
a plurality of transducers configured to receive the digital representation of the waveform and respective phase shift control signals and to generate ultrasonic waveforms based on the received digital representation and respective phase shift control signals.

21. The system of claim 20 wherein the waveform representation generator comprises a counter and is configured to generate respective sets of the first plurality of bits of the series of bit sequences by counting numbers of successive clock pulses in which the defined waveform maintains current waveform states.

22. The system of claim 20 wherein each bit sequence of the series of bit sequences corresponds to a waveform period having a duration corresponding to the number of successive clock pulses in which the defined waveform maintains the current waveform state.

23. The system of claim 20 wherein the waveform representation generator is configured to:
   determine when a boundary of a pair of adjacent waveform periods corresponds to a synchronous change of two or more signals of the plurality of binary signals;
   when it is determined that a boundary of a pair of adjacent waveform periods corresponds to a synchronous change of two or more signals of the plurality of binary signals, detect one or more repetitions of the pair of adjacent waveform periods; and
   when one or more repetitions of the pair of adjacent waveform periods is detected, increment a repetition counter associated with the pair of adjacent waveforms periods.

24. The system of claim 23 wherein when the repetition counter associated with the pair of adjacent waveform periods indicates one or more repetitions of the pair of waveform periods has been detected, the waveform representation generator is configured to:
   associate a pair of bit sequences associated with the pair of adjacent waveform periods with the repetition counter.

25. The system of claim 20 wherein the waveform representation generator is configured to receive a binary signal defining the recording period.

* * * * *